(12) United States Patent
Zhang et al.

(10) Patent No.: US 9,718,802 B2
(45) Date of Patent: Aug. 1, 2017

(54) CRYSTAL FORM OF DABIGATRAN ETEXILATE MESYLATE AND PREPARATION METHOD AND USE THEREOF

(71) Applicant: Zhejiang Hisun Pharmaceutical Co., Ltd., Taizhou (CN)

(72) Inventors: Liang Zhang, Taizhou (CN); Chuan Liu, Taizhou (CN); Jinyi Xu, Taizhou (CN); Zhaozhao Zhang, Taizhou (CN); Zhi Chen, Taizhou (CN); Jian Chai, Taizhou (CN); Zhiqing Yang, Taizhou (CN); Hairong Luo, Taizhou (CN); Xiangyang Zhang, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 15/123,378

(22) PCT Filed: Mar. 4, 2015

(86) PCT No.: PCT/CN2015/073650
§ 371 (c)(1),
(2) Date: Sep. 2, 2016

(87) PCT Pub. No.: WO2015/131829
PCT Pub. Date: Sep. 11, 2015

(65) Prior Publication Data
US 2017/0073327 A1    Mar. 16, 2017

(30) Foreign Application Priority Data
Mar. 4, 2014 (CN) .......................... 2014 1 0077142

(51) Int. Cl.
*C07D 401/12* (2006.01)
*C07C 309/04* (2006.01)
*C07C 303/44* (2006.01)
*C07D 403/12* (2006.01)

(52) U.S. Cl.
CPC .......... *C07D 401/12* (2013.01); *C07C 303/44* (2013.01); *C07C 309/04* (2013.01); *C07D 403/12* (2013.01); *C07B 2200/13* (2013.01)

(58) Field of Classification Search
None
See application file for complete search history.

(56) References Cited

U.S. PATENT DOCUMENTS

| 7,932,273 | B2 | 4/2011 | Schmid et al. |
| 2006/0276513 | A1 | 12/2006 | Hauel et al. |
| 2008/0119523 | A1* | 5/2008 | Schmid ................ C07D 401/12 514/338 |
| 2009/0042948 | A1 | 2/2009 | Sieger et al. |
| 2015/0038721 | A1 | 2/2015 | Bartra Sanmart et al. |

FOREIGN PATENT DOCUMENTS

| CN | 101189224 A | 5/2008 |
| CN | 102050815 A | 5/2011 |
| CN | 102167695 A | 8/2011 |
| CN | 102391250 A | 3/2012 |
| CN | 102858762 A | 1/2013 |
| CN | 103288800 A | 9/2013 |
| EP | 2631234 A1 | 8/2013 |
| WO | 2006114415 A2 | 11/2006 |
| WO | 2008043759 A1 | 4/2008 |
| WO | 2011110876 A1 | 9/2011 |
| WO | 2012027543 A1 | 3/2012 |
| WO | 2012044595 A1 | 4/2012 |

OTHER PUBLICATIONS

International Search Report for Application No. PCT/CN2015/073650 dated Jun. 9, 2015.

* cited by examiner

*Primary Examiner* — Timothy R Rozof
(74) *Attorney, Agent, or Firm* — Lerner, David, Littenberg, Krumholz & Mentlik, LLP (57) ABSTRACT

The present invention relates to novel crystal forms M and N of dabigatran etexilate mesylate and preparation method and uses thereof, wherein the X-Ray powder diffractogram of the crystal form M has characteristic peaks at the following $2\theta$ diffraction angles: $5.7\pm0.2°$, $6.2\pm0.2°$, $11.2\pm0.2°$, $12.4\pm0.2°$, $18.2\pm0.2°$, $21.4\pm0.2°$, $21.8\pm0.2°$ and $23.6\pm0.2°$; and the X-Ray powder diffractogram of the crystal form N has characteristic peaks at the following $2\theta$ diffraction angles: $6.0\pm0.2°$, $11.8\pm0.2°$, $18.2\pm0.2°$, $21.6\pm0.2°$, $24.4\pm0.2°$, $27.7\pm0.2°$ and $29.7\pm0.2°$. The crystal forms of the present invention have excellent properties in the aspects of leaching time, biological release, chemical stability and processing adaptability.

15 Claims, 8 Drawing Sheets

CRYSTAL FORM OF DABIGATRAN ETEXILATE MESYLATE AND PREPARATION METHOD AND USE THEREOF

CROSS REFERENCE TO RELATED APPLICATIONS

The present application is a national phase entry under 35 U.S.C. §371 of International Application No. PCT/CN2015/073650, filed Mar. 4, 2015, which claims priority from Chinese Patent Application No. 201410077142.8, filed Mar. 4, 2014, all of which are hereby incorporated herein by reference.

This application claims the priority of patent application No. 201410077142.8, entitled "CRYSTAL FORM OF DABIGATRAN ETEXILATE MESYLATE AND PREPARATION METHOD AND USE THEREOF" filed on Mar. 4, 2014.

FIELD OF THE INVENTION

The present invention belongs to the field of chemical pharmaceutical industry, more specifically, the present invention relates to the new crystal form of dabigatran etexilate mesylate and preparation method thereof, the pharmaceutical composition comprising the dabigatran etexilate mesylate and the use of preparing medicaments thereof.

BACKGROUND OF THE INVENTION

Dabigatran etexilate is a new type of thrombin inhibitors, is the prodrug of dabigatran, and it belongs to non-peptide thrombin inhibitors, and it is developed and manufactured by Boehringer Ingelheim. It was first approved by FDA in the year 2010 to use in the prevention of stroke and systemic embolism for patients with nonvalvular atrial fibrillation. At present, this indication has been approved in more than sixty countries around the world. Dabigatran etexilate will turn into dabigatran that has direct anticoagulant activity after being taken orally and through stomach and intestine absorption. Dabigatran binds to the specific binding site of the fibrin of thrombin, preventing fibrinogen from degradating into fibrin, thus preventing thrombosis. Dabigatran can be dissociated from fibrin-thrombin conjugate, and exhibits reversible anticoagulation effect.

The chemical name of dabigatran etexilate mesylate is: 3-[(2-{[4-(hexaoxycarbonylamino-imino-methyl)-phenylamino]-methyl}-1-methyl-1H-benzimidazole-5-carbonyl)-pyridine-2-yl-amino-]-ethyl propionate-mesylate.

The structural formula is as follows:

Patent document U.S. Pat. No. 7,932,273B2 discloses crystal form I, crystal form II and semihydrate of dabigatran etexilate mesylate; WO2012027543A1 discloses crystal form A, B, C, D, G, H and III of dabigatran etexilate mesylate; WO2012044595A1 discloses crystal form Ms2-A of dabigatran etexilate dimesylate; WO2011110876A1 discloses crystal form IV of dabigatran etexilate mesylate (1:1).

For drugs that present polymorphism, different crystal forms can have different physical chemical properties, including melting point, chemical stability, apparent solubility, dissolution rate, optical and mechanical properties etc., and these physical chemical properties directly determine whether a specific crystal form can formulate drugs, and they affect the quality of active pharmaceutical ingredients and formulations. Therefore, although some crystal forms of dabigatran etexilate have been disclosed in prior art, it is still necessary to develop new crystal forms with properties different from the known crystal forms and can be used in the formulations to meet the stringent requirements for preparing drugs.

SUMMARY OF THE INVENTION

One of the object of the present invention is to provide crystal form M and crystal form N of dabigatran etexilate mesylate with great chemical and physical stability. Said crystal forms have excellent properties in the aspects of leaching time, biological release, chemical stability and processing (filtration, drying, tabletting) adaptability.

The X-Ray powder diffractogram of the crystal form M of the dabigatran etexilate mesylate of the present invention has characteristic peaks at the following 2θ diffraction angles: 5.7±0.2°, 6.2±0.2°, 11.2±0.2°, 12.4±0.2°, 18.2±0.2°, 21.4±0.2°, 21.8±0.2° and 23.6±0.2°.

Furthermore, the X-Ray powder diffractogram (XRD) of the crystal form M of the dabigatran etexilate mesylate has characteristic peaks at the following 2θ diffraction angles: 5.7±0.2°, 6.2±0.2°, 11.2±0.2°, 12.4±0.2°, 16.3±0.2°, 18.2±0.2°, 21.4±0.2°, 21.8±0.2°, 22.8±0.2°, 23.6±0.2°, 25.0±0.2° and 27.3±0.2°.

Furthermore, the X-Ray powder diffractogram of the crystal form M of the dabigatran etexilate mesylate has characteristic peaks at the following 2θ diffraction angles: 5.7±0.2°, 6.2±0.2°, 8.1±0.2°, 11.2±0.2°, 12.4±0.2°, 13.0±0.2°, 16.3±0.2°, 17.1±0.2°, 18.2±0.2°, 21.4±0.2°, 21.8±0.2°, 22.8±0.2°, 23.6±0.2°, 25.0±0.2°, 27.3±0.2° and 29.0±0.2°.

Furthermore, the X-Ray powder diffractogram of the crystal form M of the dabigatran etexilate mesylate of the present invention has 2θ, d and relative intensity data shown in the table 1 below:

TABLE 1

| 2θ(°) | d(Å) | Relative intensity (%) |
|---|---|---|
| 5.7 ± 0.2 | 15.6 | 20.1 |
| 6.2 ± 0.2 | 14.2 | 24.0 |
| 8.1 ± 0.2 | 11.0 | 6.6 |
| 11.2 ± 0.2 | 7.9 | 48.9 |
| 12.4 ± 0.2 | 7.1 | 62.0 |
| 13.0 ± 0.2 | 6.8 | 16.6 |
| 16.3 ± 0.2 | 5.4 | 16.6 |
| 17.1 ± 0.2 | 5.2 | 17.0 |
| 18.2 ± 0.2 | 4.9 | 100.0 |
| 21.4 ± 0.2 | 4.2 | 69.4 |
| 21.8 ± 0.2 | 4.1 | 55.5 |
| 22.8 ± 0.2 | 3.9 | 27.1 |
| 23.6 ± 0.2 | 3.8 | 34.9 |
| 25.0 ± 0.2 | 3.6 | 31.4 |
| 27.3 ± 0.2 | 3.3 | 37.1 |
| 29.0 ± 0.2 | 3.1 | 6.1 |

Furthermore, the X-Ray powder diffractogram of the crystal form M of the dabigatran etexilate mesylate of the present invention has 2θ, d and relative intensity data shown in table 2 below:

TABLE 2

| Peak No. | 2θ(°) | d(Å) | Relative intensity (%) |
|---|---|---|---|
| 1 | 5.7 ± 0.2 | 15.6 | 20.1 |
| 2 | 6.2 ± 0.2 | 14.2 | 24.0 |
| 3 | 8.1 ± 0.2 | 11.0 | 6.6 |
| 4 | 11.2 ± 0.2 | 7.9 | 48.9 |
| 5 | 12.4 ± 0.2 | 7.1 | 62.0 |
| 6 | 13.0 ± 0.2 | 6.8 | 16.6 |
| 7 | 13.7 ± 0.2 | 6.5 | 10.5 |
| 8 | 14.8 ± 0.2 | 6.0 | 5.2 |
| 9 | 16.3 ± 0.2 | 5.4 | 16.6 |
| 10 | 17.1 ± 0.2 | 5.2 | 17.0 |
| 11 | 18.2 ± 0.2 | 4.9 | 100.0 |
| 12 | 20.0 ± 0.2 | 4.4 | 3.5 |
| 13 | 21.4 ± 0.2 | 4.2 | 69.4 |
| 14 | 21.8 ± 0.2 | 4.1 | 55.5 |
| 15 | 22.1 ± 0.2 | 4.0 | 22.3 |
| 16 | 22.8 ± 0.2 | 3.9 | 27.1 |
| 17 | 23.6 ± 0.2 | 3.8 | 34.9 |
| 18 | 25.0 ± 0.2 | 3.6 | 31.4 |
| 19 | 25.6 ± 0.2 | 3.5 | 8.3 |
| 20 | 27.3 ± 0.2 | 3.3 | 37.1 |
| 21 | 27.6 ± 0.2 | 3.2 | 13.5 |
| 22 | 29.0 ± 0.2 | 3.1 | 6.1 |
| 23 | 30.5 ± 0.2 | 2.9 | 6.1 |
| 24 | 32.8 ± 0.2 | 2.7 | 8.3 |
| 25 | 33.8 ± 0.2 | 2.7 | 5.7 |

Figure 1:
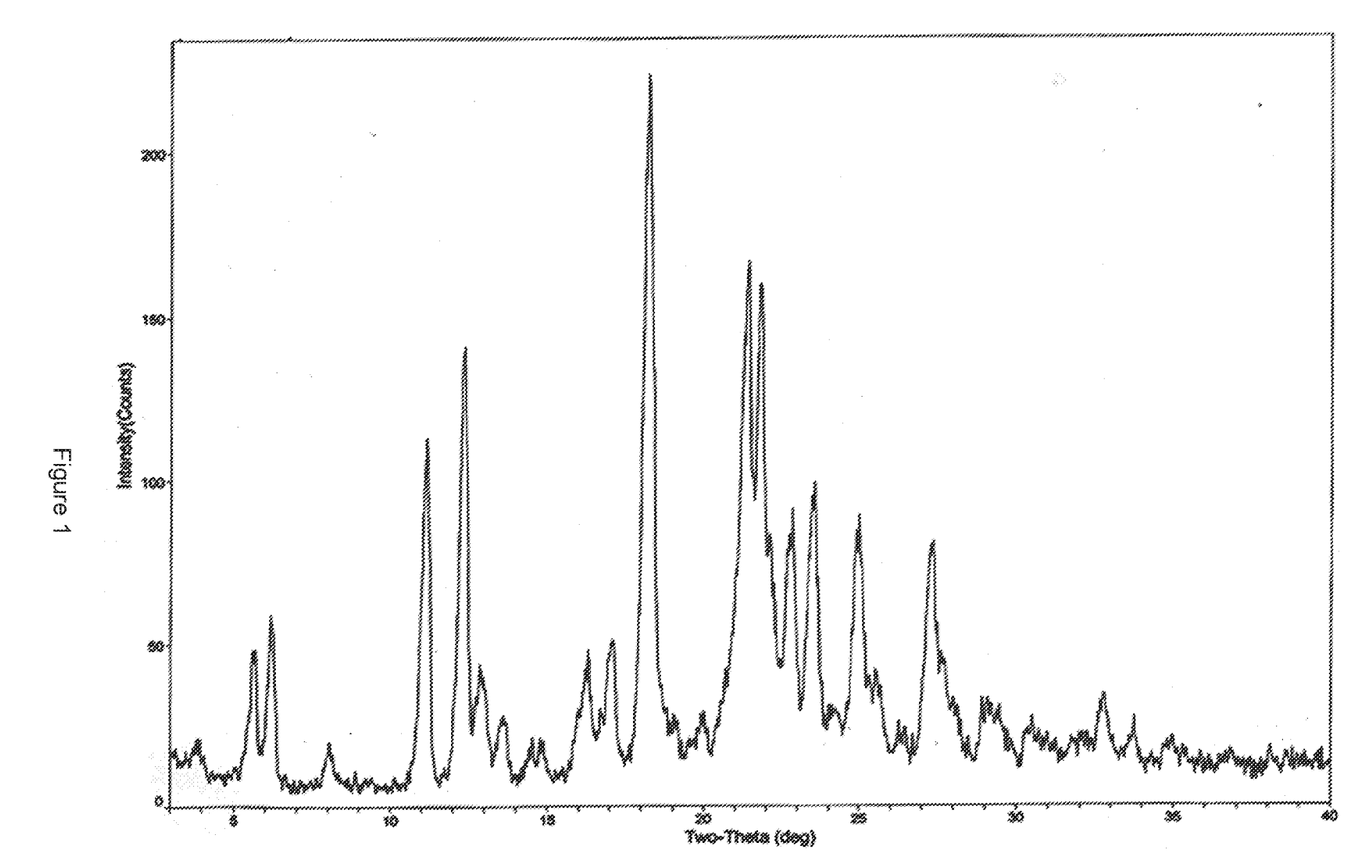
FIG. 1 is the X-Ray powder diffractogram of the crystal form M of the dabigatran etexilate mesylate obtained in example 1.

Unrestrictedly, the crystal form M of the dabigatran etexilate mesylate of the present invention has a X-Ray powder diffractogram as shown in FIG. 1.

In addition, the crystal form M of the dabigatran etexilate mesylate of the present invention can be characterized by the infrared absorption spectrum measured by KBr pellet, it has absorption peaks at about 3433.73 cm$^{-1}$, 3319.45 cm$^{-1}$, 2957.35 cm$^{-1}$, 2931.08 cm$^{-1}$, 2862.04 cm$^{-1}$, 1743.33 cm$^{-1}$, 1732.42 cm$^{-1}$, 1650.10 cm$^{-1}$, 1614.11 cm$^{-1}$, 1586.80 cm$^{-1}$, 1572.31 cm$^{-1}$, 1472.02 cm$^{-1}$, 1435.21 cm$^{-1}$, 1384.33 cm$^{-1}$, 1319.30 cm$^{-1}$, 1231.52 cm$^{-1}$, 1045.54 cm$^{-1}$, 951.65 cm$^{-1}$, 774.31 cm$^{-1}$, 749.63 cm$^{-1}$, 554.38 cm$^{-1}$, 527.97 cm$^{-1}$.

Furthermore, the infrared absorption spectrum of the crystal form M of the dabigatran etexilate mesylate has characteristic peaks at about 3433.73 cm$^{-1}$, 3319.45 cm$^{-1}$, 3067.58 cm$^{-1}$, 2957.35 cm$^{-1}$, 2931.08 cm$^{-1}$, 2862.04 cm$^{-1}$, 1743.33 cm$^{-1}$, 1732.42 cm$^{-1}$, 1650.10 cm$^{-1}$, 1614.11 cm$^{-1}$, 1586.80 cm$^{-1}$, 1572.31 cm$^{-1}$, 1547.89 cm$^{-1}$, 1514.12 cm$^{-1}$, 1472.02 cm$^{-1}$, 1435.21 cm$^{-1}$, 1414.83 cm$^{-1}$, 1384.33 cm$^{-1}$, 1319.30 cm$^{-1}$, 1285.88 cm$^{-1}$, 1231.52 cm$^{-1}$, 1180.00 cm$^{-1}$, 1164.18 cm$^{-1}$, 1128.71 cm$^{-1}$, 1045.54 cm$^{-1}$, 1018.39 cm$^{-1}$, 1006.87 cm$^{-1}$, 990.23 cm$^{-1}$, 951.65 cm$^{-1}$, 884.04 cm$^{-1}$, 863.24 cm$^{-1}$, 836.54 cm$^{-1}$, 774.31 cm$^{-1}$, 749.63 cm$^{-1}$, 715.61 cm$^{-1}$, 663.14 cm$^{-1}$, 624.45 cm$^{-1}$, 554.38 cm$^{-1}$, 527.97 cm$^{-1}$, 506.96 cm$^{-1}$, 448.39 cm$^{-1}$, 414.70 cm$^{-1}$.

Figure 2:
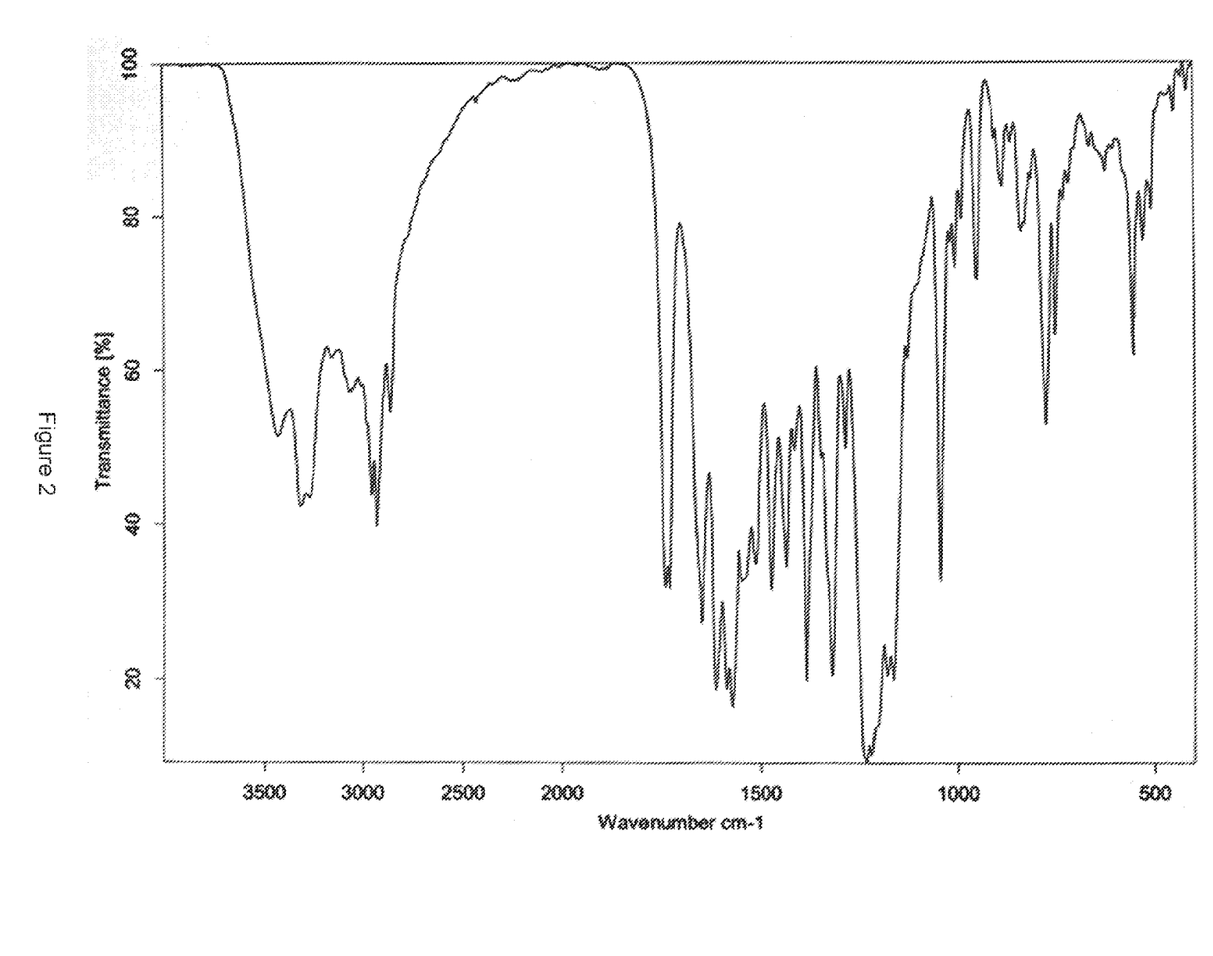
FIG. 2 is the infrared absorption spectrum of the crystal form M of the dabigatran etexilate mesylate obtained in example 1.

Unrestrictedly, the crystal form M of the dabigatran etexilate mesylate of the present invention has an infrared absorption spectrum as shown in FIG. 2.

The Differential Scanning calorimetry (DSC) thermogram of the crystal form M of the dabigatran etexilate mesylate of the present invention has a maximum absorption peak within the range of 145-150° C.

Figure 3:
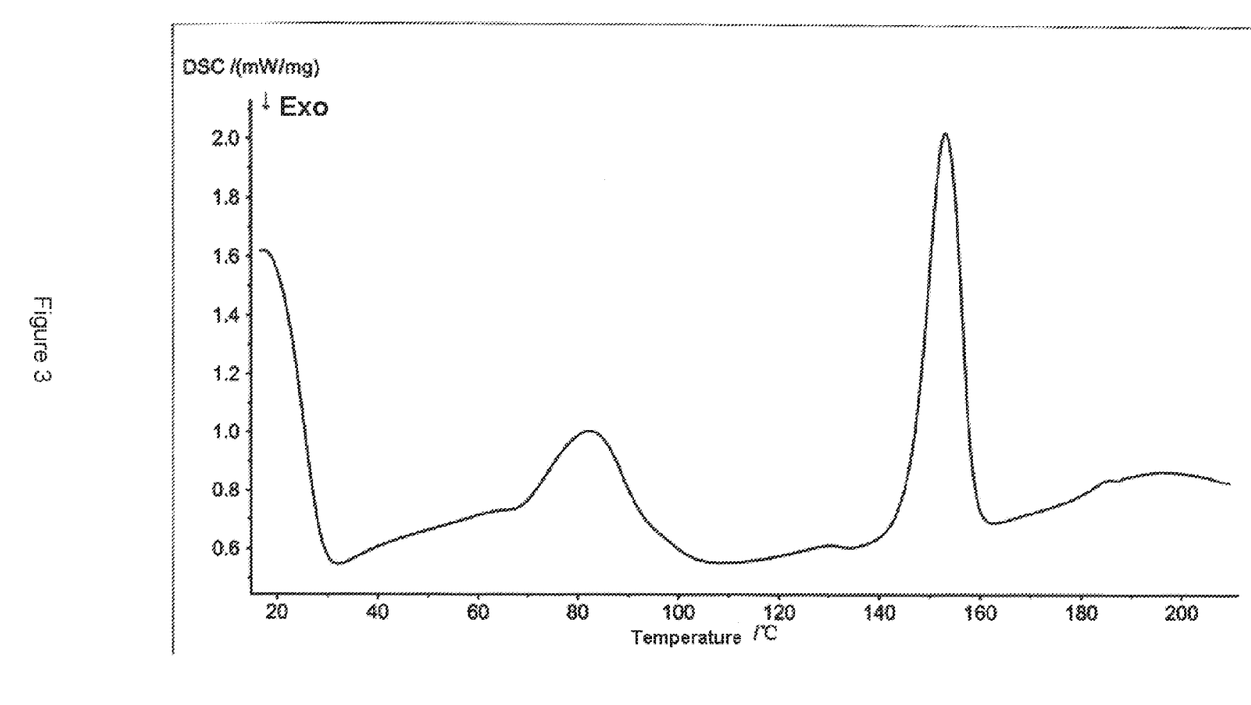
FIG. 3 is the DSC thermogram of the crystal form M of the dabigatran etexilate mesylate obtained in example 1.

Unrestrictedly, the crystal form M of the dabigatran etexilate mesylate of the present invention has a DSC thermogram as shown in FIG. 3.

Figure 4:
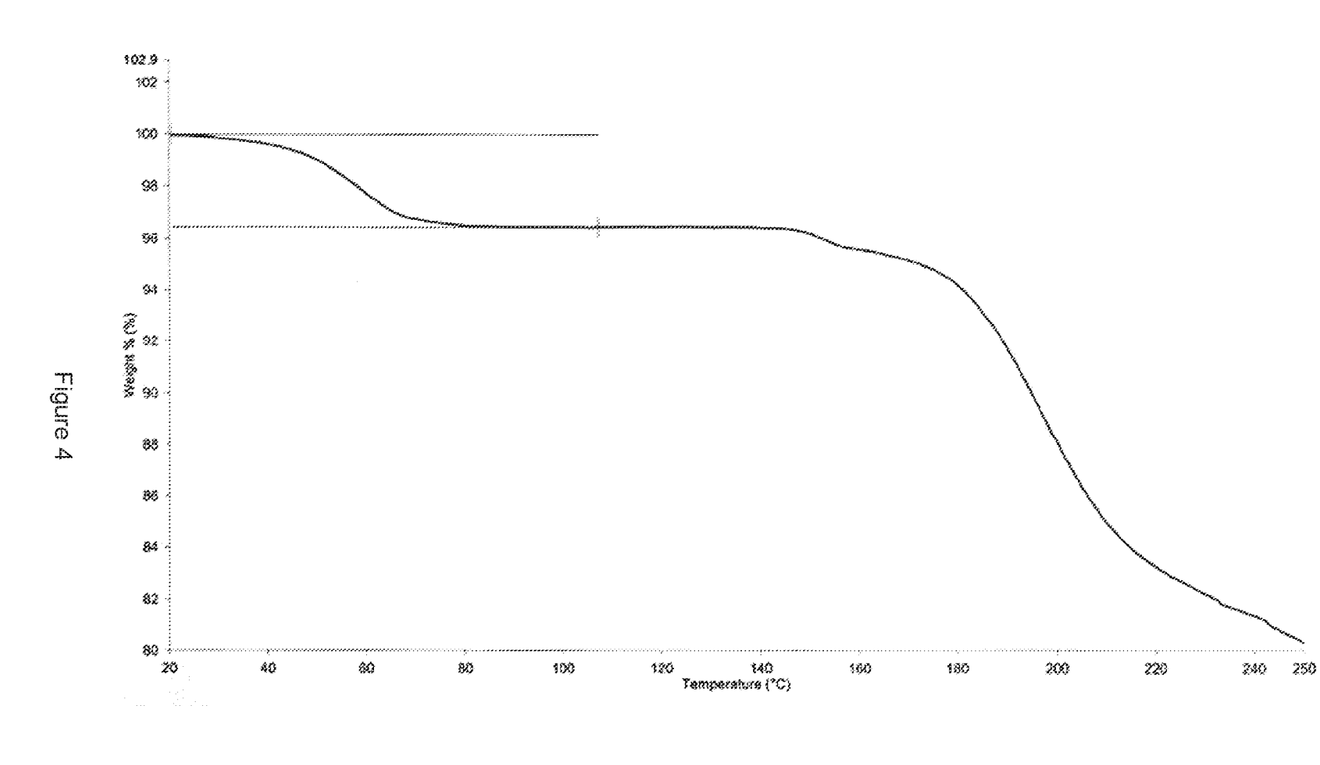
FIG. 4 is the TGA thermogram of the crystal form M of the dabigatran etexilate mesylate obtained in example 1.

Unrestrictedly, the crystal form M of the dabigatran etexilate mesylate of the present invention has a TGA thermogram as shown in FIG. 4. According to the result obtained by TGA thermogram and a moisture measuring apparatus (apparatus model: METTLER TOLEDO DL31 Karl Fischer Titrator), it is estimated that the crystal form M has 1.5 hydrate water.

The other object of the present invention is to provide a method for preparing the crystal form M of the dabigatran etexilate mesylate, said method comprising:

method one:

(1) dabigatran etexilate mesylate is added into an ethanol/ethyl acetate mixed solvent with the volume ratio of ethanol/ethyl acetate of 1:2; wherein the weight-to-volume ratio of the dabigatran etexilate mesylate to ethanol/ethyl acetate mixed solvent is 1:40; and the molar ratio of the total water content in the obtained system to the dabigatran etexilate mesylate is controlled to 1.5-10:1;

(2) The temperature is increased to 50-60° C., and the system is stirred continuously for 30-60 min to dissolve the dabigatran etexilate mesylate;

(3) the system is filtered and the filtrate is stirred to decrease the temperature to 0-25° C.;

(4) crystallization is performed at 0-25° C. for 2-18 h;

(5) crystal form M of dabigatran etexilate mesylate is obtained by filtration.

In said method, the unit of the weight-to-volume ratio of the dabigatran etexilate mesylate to ethanol/ethyl acetate mixed solvent can be g/ml, Kg/L etc., which depends on the specific operation scale; the source of the total water content of the obtained system can include the trace amount of water contained in the dabigatran etexilate mesylate raw material, the water contained in the ethanol/ethyl acetate mixed solvent and the water introduced naturally from the environment, such as air; if the water content contained in the system cannot meet the above requirement of molar ratio, then the water content should be adjusted to the allowed range by methods such as adding water or drying material or removing water etc.; the water content in the system can be determined by common methods in the art, such as it can be determined by a moisture meter, or it can be estimated by the theoretical water content in the known raw material and solvents.

Preferably, the rate of decreasing the temperature while stirring can be controlled to 3-20° C./h, more preferably 10° C./h.

Or method two:

(1) dabigatran etexilate mesylate is added into an alcohol, alcohol/ketone mixed solvent or alcohol/ester mixed solvent; and the molar ratio of the total water content in the obtained system to the dabigatran etexilate mesylate is controlled to about 1.5-10:1;

(2) The temperature is increased to 50-60° C., and the system is stirred continuously for 30-60 min to dissolve the dabigatran etexilate mesylate;

(3) the system is filtered and the filtrate is stirred to decrease the temperature to 0-5° C.;

(4) seed crystals are added;

(5) crystallization is performed at 0-5° C., crystal form M of dabigatran etexilate mesylate is obtained by filtration.

In the above method, the total water content of the obtained system in step (1) can include the trace amount of water contained in the dabigatran etexilate mesylate raw material, the water contained in the solvent and the water introduced naturally from the environment, such as air; if the total water content contained in the system cannot meet the above requirement of molar ratio, then the water content should be adjusted to the allowed range by methods such as adding water or drying material or removing water etc.; similarly, the water content in the system can be determined by common methods in the art, such as it can be determined by a moisture meter, or it can be estimated by the theoretical water content in the known raw material and solvents.

The alcohol in the solvent used in step (1) is C1-C4 alcohol, preferably methanol, ethanol, isopropanol or n-butyl alcohol; the ketone is C3-C5 ketone, preferably acetone, butanone or pentanone; the ester is C3-C6 ester, preferably methyl acetate, ethyl acetate or butyl acetate;

the preferred solvent is ethanol, ethanol/acetone mixed solvent, or ethanol/ethyl acetate mixed solvent;

when ethanol is used as solvent, the preferred weight-to-volume ratio of dabigatran etexilate mesylate to ethanol solvent is 1:10-100, more preferably 1:10-20;

when ethanol/acetone mixed solvent is used, the preferred weight-to-volume ratio of dabigatran etexilate mesylate to ethanol/acetone mixed solvent is 1:10-100, more preferably 1:10-30; wherein the volume ratio (v/v) of ethanol to acetone is preferably 1:0.1-20, more preferably 1:0.5-5;

when ethanol/ethyl acetate mixed solvent is used, the preferred weight-to-volume ratio of dabigatran etexilate mesylate to ethanol/ethyl acetate mixed solvent is 1:10-100, more preferably 1:10-30; wherein the volume ratio (v/v) of ethanol to ethyl acetate is preferably 1:0.1-20, more preferably 1:0.5-5;

in the method, the unit of the weight-to-volume ratio of the dabigatran etexilate mesylate to the corresponding solvent can be g/ml, Kg/L etc., which depends on the specific operation scale;

preferably, the rate of decreasing the temperature while stirring in step (3) can be controlled to 20-80° C./h, more preferably 40-60° C./h;

the seed crystals in step (4) can be seed crystals of crystal form M, which can be the crystal form M prepared according to the method one, or can be the crystal form M obtained according to the method two;

The time for crystallization is preferably 1-18 hours, more preferably 1-10 hours.

The dabigatran etexilate mesylate raw material in the method of the present invention are commercially available, or it can be prepared according to known method, such as the method mentioned in the patent document U.S. Pat. No. 7,932,273B2, said document is incorporated herein by reference. There's no special limitations for the solvent used in the present invention, the solvent can be common commercially available solvent, for example, the ethanol can be commercially available ethanol, comprising industrial ethanol, absolute ethanol, chromatographic ethanol etc.; the solvent can be used as long as the water content in the system can meet the requirement of the method when the system is constructed.

The X-Ray powder diffractogram (XRD) of the crystal form N of the dabigatran etexilate mesylate of the present invention has characteristic peaks at the following 2θ diffraction angles: 6.0±0.2°, 11.8±0.2°, 18.2±0.2°, 21.6±0.2°, 24.4±0.2°, 27.7±0.2° and 29.7±0.2°.

Furthermore, the X-Ray powder diffractogram of the crystal form N of the dabigatran etexilate mesylate has characteristic peaks at the following 2θ diffraction angles: 6.0±0.2°, 10.7±0.2°, 11.8±0.2°, 16.1±0.2°, 18.2±0.2°, 20.3±0.2°, 21.6±0.2°, 24.4±0.2°, 27.7±0.2° and 29.7±0.2°.

Furthermore, the X-Ray powder diffractogram of the crystal form N of the dabigatran etexilate mesylate of the present invention has 2θ data shown in the table 3 below:

TABLE 3

| Peak No. | 2θ(°) | d(Å) | Relative intensity (%) |
|---|---|---|---|
| 1 | 6.0 ± 0.2 | 14.8 | 23.0 |
| 2 | 10.7 ± 0.2 | 8.3 | 10.4 |
| 3 | 11.8 ± 0.2 | 7.5 | 64.8 |
| 4 | 16.1 ± 0.2 | 5.5 | 4.3 |
| 5 | 18.2 ± 0.2 | 4.9 | 39.6 |
| 6 | 20.3 ± 0.2 | 4.4 | 7.0 |
| 7 | 21.6 ± 0.2 | 4.1 | 100.0 |
| 8 | 24.4 ± 0.2 | 3.6 | 44.3 |
| 9 | 27.7 ± 0.2 | 3.2 | 17.0 |
| 10 | 29.7 ± 0.2 | 3.0 | 10.9 |

Figure 5:
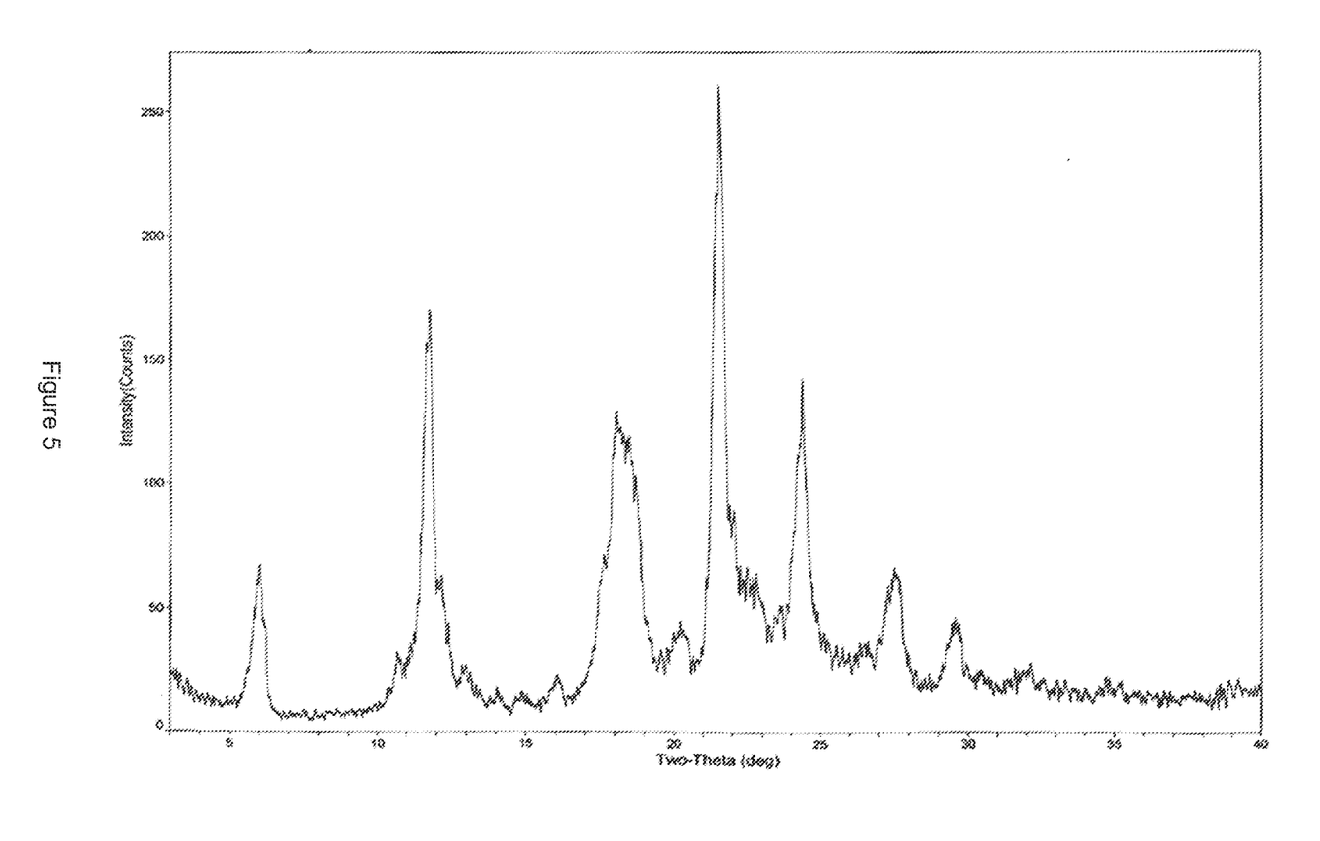
FIG. 5 is the X-Ray powder diffractogram of the crystal form N of the dabigatran etexilate mesylate obtained in example 10.

Unrestrictedly, the crystal form N of the dabigatran etexilate mesylate of the present invention has a X-Ray powder diffractogram as shown in FIG. 5.

In addition, the crystal form N of the dabigatran etexilate mesylate of the present invention can be characterized by the infrared absorption spectrum measured by KBr pellet, it has absorption peaks at about 3425.18 $cm^{-1}$, 3304.94 $cm^{-1}$, 2956.79 $cm^{-1}$, 2933.09 $cm^{-1}$, 2861.93 $cm^{-1}$, 1741.76 $cm^{-1}$, 1647.10 $cm^{-1}$, 1613.66 $cm^{-1}$, 1585.42 $cm^{-1}$, 1571.90 $cm^{-1}$, 1540.02 $cm^{-1}$, 1516.58 $cm^{-1}$, 1471.95 $cm^{-1}$, 1435.51 $cm^{-1}$, 1384.16 $cm^{-1}$, 1318.97 $cm^{-1}$, 1231.35 $cm^{-1}$, 1213.37 $cm^{-1}$, 1165.25 $cm^{-1}$, 1100.00 $cm^{-1}$, 1039.60 $cm^{-1}$, 950.09 $cm^{-1}$, 828.47 $cm^{-1}$, 771.70 $cm^{-1}$, 750.44 $cm^{-1}$, 555.24 $cm^{-1}$, 525.04 $cm^{-1}$.

Furthermore, the infrared absorption spectrum of the crystal form N of the dabigatran etexilate mesylate has absorption peaks at about 3425.18 $cm^{-1}$, 3304.94 $cm^{-1}$, 3067.26 $cm^{-1}$, 2956.79 $cm^{-1}$, 2933.09 $cm^{-1}$, 2861.93 $cm^{-1}$, 2426.21 $cm^{-1}$, 1741.76 $cm^{-1}$, 1647.10 $cm^{-1}$, 1613.66 $cm^{-1}$, 1585.42 $cm^{-1}$, 1571.90 $cm^{-1}$, 1540.02 $cm^{-1}$, 1516.58 $cm^{-1}$, 1471.95 $cm^{-1}$, 1435.51 $cm^{-1}$, 1384.16 $cm^{-1}$, 1318.97 $cm^{-1}$, 1287.42 $cm^{-1}$, 1231.35 $cm^{-1}$, 1213.37 $cm^{-1}$, 1165.25 $cm^{-1}$, 1100.00 $cm^{-1}$, 1068.76 $cm^{-1}$, 1039.60 $cm^{-1}$, 1007.05 $cm^{-1}$, 992.19 $cm^{-1}$, 950.09 $cm^{-1}$, 903.66 $cm^{-1}$, 880.99 $cm^{-1}$, 828.47 $cm^{-1}$, 771.70 $cm^{-1}$, 750.44 $cm^{-1}$, 623.24 $cm^{-1}$, 555.24 $cm^{-1}$, 525.04 $cm^{-1}$, 506.80 $cm^{-1}$, 414.45 $cm^{-1}$.

Figure 6:
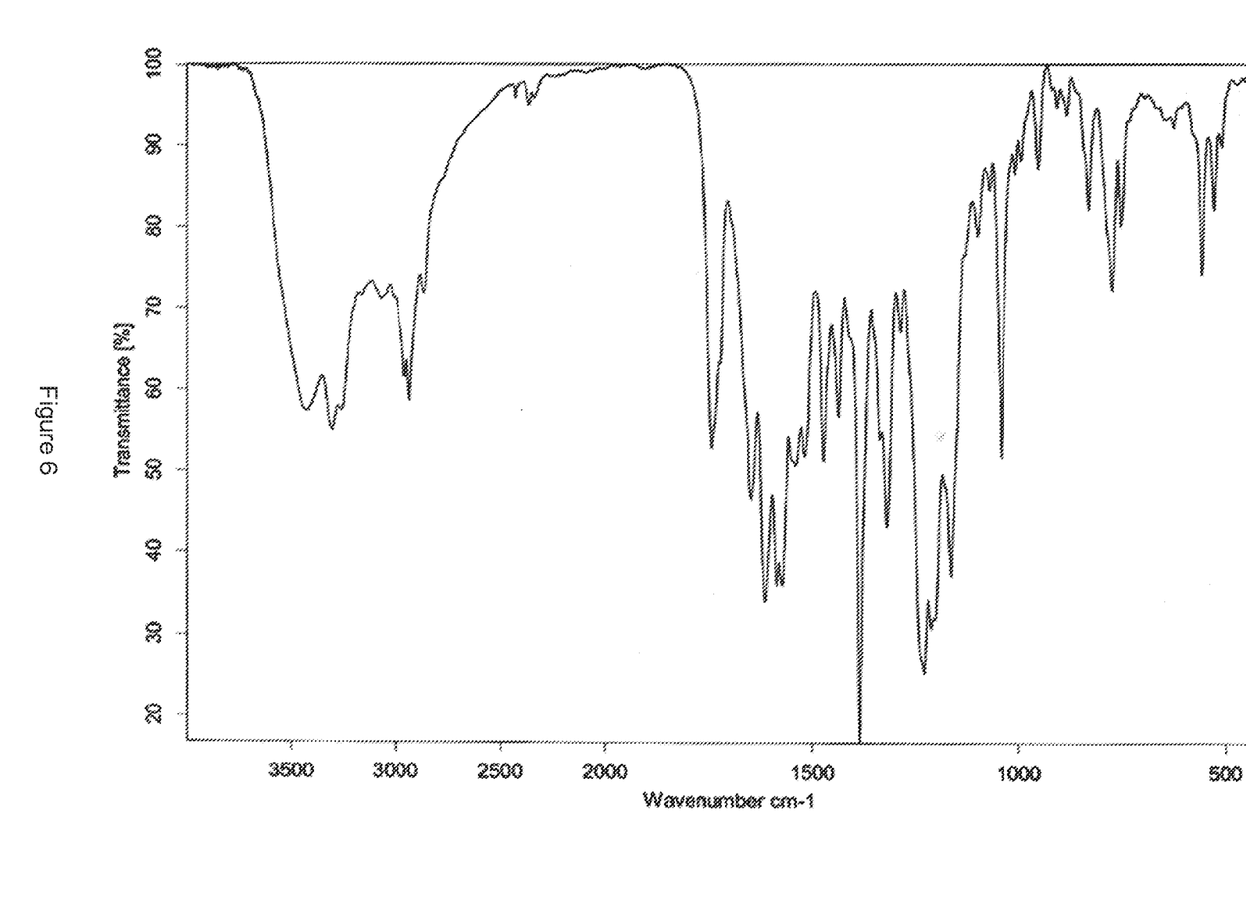
FIG. 6 is the infrared absorption spectrum of the crystal form N of the dabigatran etexilate mesylate obtained in example 10.

Unrestrictedly, the crystal form N of the dabigatran etexilate mesylate of the present invention has an infrared absorption spectrum as shown in FIG. 6.

The Differential Scanning calorimetry (DSC) thermogram of the crystal form N of the dabigatran etexilate mesylate of the present invention has a maximum absorption peak at the range of 145-150° C.

Figure 7:
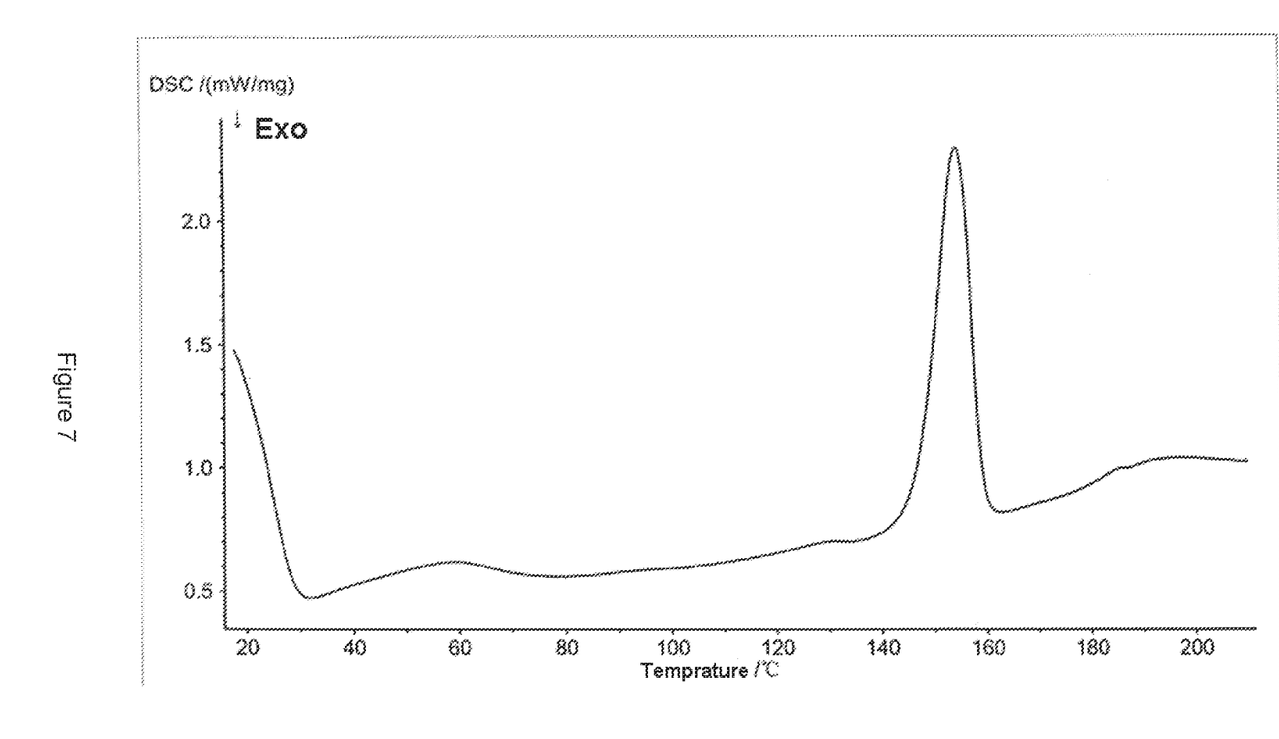
FIG. 7 is the DSC thermogram of the crystal form N of the dabigatran etexilate mesylate obtained in example 10.

Unrestrictedly, the crystal form N of the dabigatran etexilate mesylate of the present invention has a DSC thermogram as shown in FIG. 7.

Figure 8:
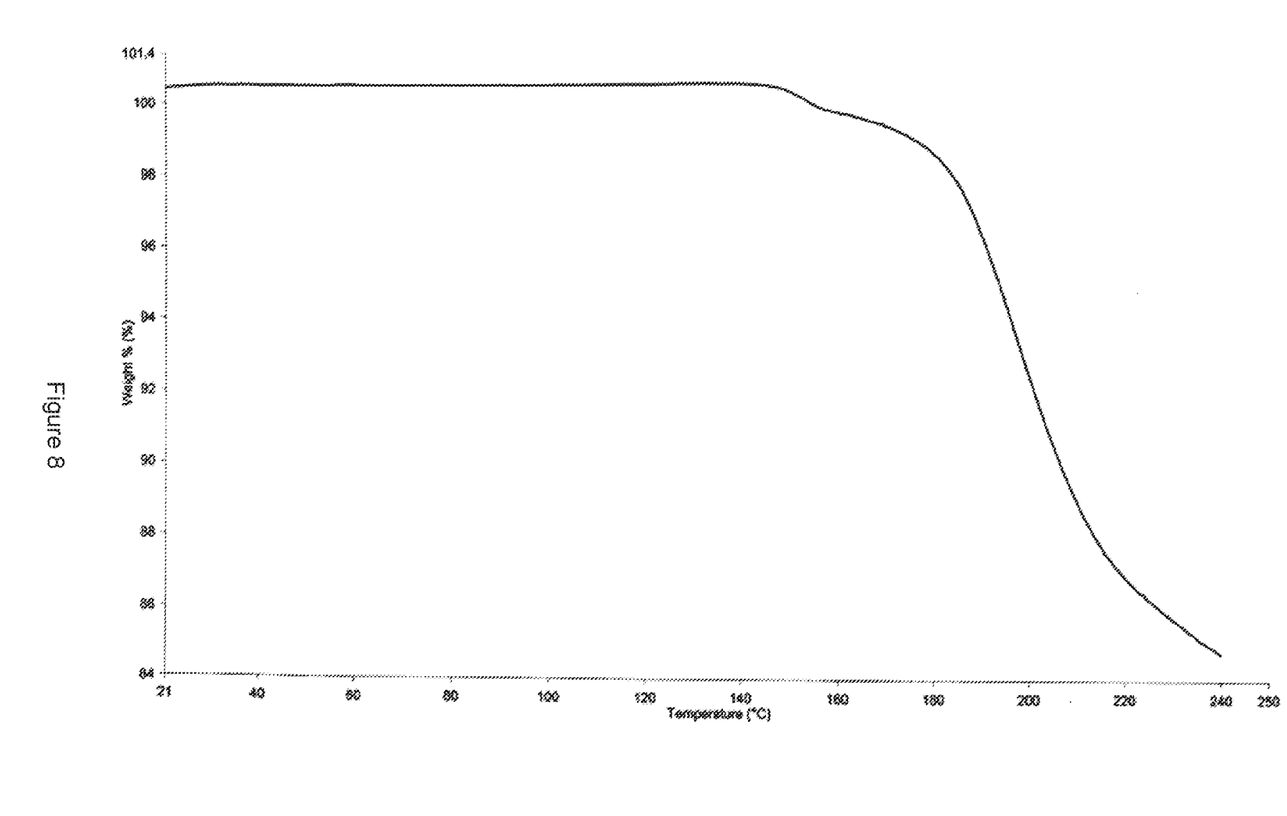
FIG. 8 is the TGA thermogram of the crystal form N of the dabigatran etexilate mesylate obtained in example 10.

Unrestrictedly, the crystal form N of the dabigatran etexilate mesylate of the present invention has a TGA thermogram as shown in FIG. 8. According to the result obtained by TGA and a moisture measuring apparatus, it is estimated that the crystal form N is an anhydride.

The other object of the present invention is to provide a method for preparing the crystal form N of the dabigatran etexilate mesylate, said method comprising the following steps:

The crystal form M of the dabigatran etexilate mesylate is dried under a vacuum degree of −0.06 Mpa-−0.1 Mpa, the temperature is preferably 20-50° C.; the time is preferably 10-100 hours to allow the form transformed into crystal form N.

In the present invention, the purities of the crystal forms M and N are all above 99.5%.

In another aspect, the present invention also provides a pharmaceutical composition comprising therapeutically effective amount of crystal form M and/or N of the dabigatran etexilate mesylate as active ingredients; preferably, in the pharmaceutical composition, the crystal form M and/or N of the dabigatran etexilate mesylate can be mixed with one or more pharmaceutically acceptable solid or liquid diluents and/or excipients, and the mixture can be made into a Galenic formulation.

The present invention also provides use of the crystal form M and/or N of the dabigatran etexilate mesylate in the preparation of anticoagulant medicament, and method of anticoagulation by using the medicament. Wherein, the medicament can be used to prolong the thrombin time, inhibit the related thrombin and the related serine protease.

Unless stated otherwise, the "stir" in the method of the present invention can be common methods in the art, such as the stirring method comprises magnetic stirring, mechanical stirring, the stirring rate is 50-300 rpm/min, preferably 100-200 rpm/min.

It should be emphasized that the meaning or the intended scope of protection of the values or the endpoints of the values mentioned in the technical solution of the present invention is not limited to the number itself, those skilled in the art should understand that it contains allowable error range widely acceptable in the art, such as experimental error, measurement error, statistical error and random error etc., and the scope of these errors should be contained in the scope of the present invention.

The inventors of the present invention have found the new crystal forms M and N of the dabigatran etexilate mesylate through a large sum of studies, the crystal forms have good solubility, and the crystallization process is simply, easy to operate and has little environmental pollution, industrial production of the forms can be realized. And the medicament of the crystal forms of the present invention has the advantages of high purity, good physical and chemical properties, good chemical stability and reproducible processing (filtration, drying, dissolution and tabletting), and has a good dissolution rate compared with other pharmaceutical formulations. In addition, the crystal form N of the dabigatran etexilate mesylate of the present invention has a very good stability in 95% ethanol solution, thus it has a certain advantage in the manufacturing of medicaments through formulation.

DETAILED DESCRIPTION OF THE INVENTION

The present invention will be further illustrated by the examples below, and it is not limited to the following examples.

The dabigatran etexilate mesylate crude products used in the following examples are the crystal form I prepared by the method of example 1 of the patent document U.S. Pat. No. 7,932,273B2.

In the following examples and tests, the powder X-ray diffractometer and the test conditions are: X-ray diffractomer model Rigaku D/max-2200 Cu target; operation method: scan rate 4°/min, scan width 0.01°.

The infrared spectrophotometer and the test conditions are: infrared spectrophotometer model: BRWKER VECTOR 22; operation method: KBr pellet method, scan range 400-4000 cm$^{-1}$.

DSC test conditions are: DSC instrument model: NETZSCH DSC200 F3 Maia; operation method: heating rate 10° C./min, temperature range: 30-250° C.

TGA test conditions are: TGA instrument model: PerkinElmer TGA400; operation method: heating rate 10° C./min, temperature range: 30-300° C.

Liquid chromatography test conditions are: chromatographic column is Merck Purospher®STAR RP-18 endcapped 250×4.6 mm, 5 μm; mobile phase A: acetonitrile, mobile phase B: 4 ml phosphoric acid added in 1 L water, the pH is adjusted to 3.5 by triethylamine; detecting wavelength: 310 nm; flow rate: 1 ml/min; sample load: 10 μl; column temperature: 30° C., liquid chromatography conditions are shown in table 4:

TABLE 4

| t(min) | A(%) | B(%) |
| --- | --- | --- |
| 0 | 30 | 70 |
| 30 | 60 | 40 |
| 50 | 60 | 40 |

Example 1

1 g dabigatran etexilate mesylate crude product (HPLC purity >99%) was dissolved in 40 ml ethanol and ethyl acetate mixed solution (ethanol:ethyl acetate=1:2, the content of ethanol was >99.5%, the content of ethyl acetate was >99.5%), the molar ratio of the water content in the system to the dabigatran etexilate mesylate was 1.5:1; the temperature was increased to 50° C., the solution was stirred continuously for 30 min to dissolve the dabigatran etexilate mesylate; then the solution was filtered, and the stirring rate was controlled to 170 rpm/min, the temperature of the filtrate was decreased to 25° C. at a rate of 10° C./h, and crystallization was performed under 25° C. while stirring for 4 h, the solution was filtered and vacuum dried at 20° C., 0.30 g crystal was obtained, HPLC=99.6%.

The X-Ray powder diffractogram, the infrared absorption spectrum, the DSC thermogram and the TGA thermogram of the crystal form are shown in FIGS. 1-4, in the present invention, it is named as crystal form M of the dabigatran etexilate mesylate.

Example 2

1 g dabigatran etexilate mesylate crude product (HPLC purity >99%) was dissolved in 40 ml ethanol and ethyl acetate mixed solution (ethanol:ethyl acetate=1:2, the content of ethanol was >99.5%, the content of ethyl acetate was >99.5%), the molar ratio of the water content in the system to the dabigatran etexilate mesylate was 5:1; the temperature was increased to 50° C., the solution was stirred continuously for 30 min to dissolve the dabigatran etexilate mesylate; then the solution was filtered, and the stirring rate was controlled to 170 rpm/min, the temperature of the filtrate was decreased to 25° C. at a rate of 10° C./h, and crystallization was performed under 25° C. while stirring for 4 h, the solution was filtered and vacuum dried at 20° C., 0.32 g crystal was obtained, HPLC=99.7%. The product was determined to be crystal form M through X-ray powder diffraction (XRD).

Example 3

1 g dabigatran etexilate mesylate crude product (HPLC purity >99%) was dissolved in 40 ml ethanol and ethyl acetate mixed solution (ethanol:ethyl acetate=1:2, the content of ethanol was >95%, the content of ethyl acetate was >99.5%), the molar ratio of the water content in the system to the dabigatran etexilate mesylate was 10:1; the temperature was increased to 50° C., the solution was stirred continuously for 30 min to dissolve the dabigatran etexilate mesylate; then the solution was filtered, and the stirring rate was controlled to 170 rpm/min, the temperature of the filtrate was decreased to 25° C. at a rate of 10° C./h, and crystallization was performed under 25° C. while stirring for 4 h, the solution was filtered and vacuum dried at 20° C., 0.31 g crystal was obtained, HPLC=99.6%. The product was determined to be crystal form M through X-ray powder diffraction (XRD).

Example 4

1 g dabigatran etexilate mesylate crude product (HPLC purity >99%) was dissolved in 18 ml methanol and acetone mixed solution (methanol:acetone=1:4, the content of methanol was >98.5%, the content of acetone was >98.5%), the molar ratio of the water content in the system to the dabigatran etexilate mesylate was about 5:1; the temperature was increased to 55° C., the solution was stirred continuously for 30 min to dissolve the dabigatran etexilate mesylate; then the solution was filtered, and the stirring rate was controlled to 170 rpm/min, the temperature of the filtrate was decreased to 5° C. at a rate of 50° C./h, seed crystals of the Crystal form M prepared in example 1 were added, and crystallization was performed under 5° C. while stirring for 5 h, the solution was filtered and vacuum dried at 20° C., 0.50 g crystal was obtained, HPLC=99.7%. The product was determined to be crystal form M through XRD.

Example 5

1 g dabigatran etexilate mesylate crude product (HPLC purity >99%) was dissolved in 25 ml methanol and acetone mixed solution (methanol:acetone=1:6, the content of methanol was >98.5%, the content of acetone was >98.5%), the molar ratio of the water content in the system to the dabigatran etexilate mesylate was about 3:1; the temperature was increased to 55° C., the solution was stirred continuously for 30 min to dissolve the dabigatran etexilate mesylate; then the solution was filtered, and the stirring rate was controlled to 170 rpm/min, the temperature of the filtrate was decreased to 2° C. at a rate of 50° C./h, seed crystals of the crystal form M prepared in example 1 were added, and crystallization was performed under 2° C. while stirring for 8 h, the solution was filtered and vacuum dried at 20° C., 0.70 g crystal was obtained, HPLC=99.6%. The product was determined to be crystal form M through XRD.

Example 6

1 g dabigatran etexilate mesylate crude product (HPLC purity >99%) was dissolved in 20 ml ethanol and acetone mixed solution (ethanotacetone=1:1, the content of ethanol was >99.5%, the content of acetone was >98.5%), the molar ratio of the water content in the system to the dabigatran etexilate mesylate was about 6:1; the temperature was increased to 60° C., the solution was stirred continuously for 30 min to dissolve the dabigatran etexilate mesylate; then the solution was filtered, and the stirring rate was controlled to 170 rpm/min, the temperature of the filtrate was decreased to 0° C. at a rate of 60° C./h, seed crystals of the crystal form M prepared in example 1 were added, and crystallization was performed under 0° C. while stirring for 8 h, the solution was filtered and vacuum dried at 20° C., 0.71 g crystal was obtained, HPLC=99.8%. The product was determined to be crystal form M through XRD.

Example 7

1 g dabigatran etexilate mesylate crude product (HPLC purity >99%) was dissolved in 25 ml ethanol and acetone mixed solution (ethanol:acetone=1:2, the content of ethanol was >99.5%, the content of acetone was >98.5%), the molar ratio of the water content in the system to the dabigatran etexilate mesylate was about 4:1; the temperature was increased to 50° C., the solution was stirred continuously for 30 min to dissolve the dabigatran etexilate mesylate; then the solution was filtered, and the stirring rate was controlled to 170 rpm/min, the temperature of the filtrate was decreased to 5° C. at a rate of 45° C./h, seed crystals of the crystal form M prepared in example 1 were added, and crystallization was performed under 5° C. while stirring for 18 h, the solution was filtered and vacuum dried at 20° C., 0.67 g crystal was obtained, HPLC=99.8%. The product was determined to be crystal form M through XRD.

Example 8

1 g dabigatran etexilate mesylate crude product (HPLC purity >99%) was dissolved in 15 ml ethanol and ethyl acetate mixed solution (ethanol:ethyl acetate=1:1, the content of ethanol was >95%, the content of ethyl acetate was >98.5%), the molar ratio of the water content in the system to the dabigatran etexilate mesylate was about 8:1; the temperature was increased to 50° C., the solution was stirred continuously for 30 min to dissolve the dabigatran etexilate mesylate; then the solution was filtered, and the stirring rate was controlled to 170 rpm/min, the temperature of the filtrate was decreased to 5° C. at a rate of 45° C./h, seed crystals of the crystal form M prepared in example 1 were added, and crystallization was performed under 5° C. while stirring for 12 h, the solution was filtered and vacuum dried at 20° C., 0.73 g crystal was obtained, HPLC=99.7%. The product was determined to be crystal form M through XRD.

Example 9

1 g dabigatran etexilate mesylate crude product (HPLC purity >99%) was dissolved in 20 ml ethanol, the content of ethanol was >99.5%, the molar ratio of the water content in the system to the dabigatran etexilate mesylate was about 3:1; the temperature was increased to 50° C., the solution was stirred continuously for 30 min to dissolve the dabigatran etexilate mesylate; then the solution was filtered, and the stirring rate was controlled to 170 rpm/min, the temperature of the filtrate was decreased to 5° C. at a rate of 45° C./h, seed crystals of the crystal form M prepared in example 1 were added, and crystallization was performed under 5° C. while stirring for 5 h, the solution was filtered and vacuum dried at 20° C., 0.42 g crystal was obtained, HPLC=99.6%. The product was determined to be crystal form M through XRD.

The X-Ray powder diffractograms of the products obtained in examples 2-9 are the same as that of example 1, thus they won't be mentioned here.

Example 10

1 g dabigatran etexilate mesylate crystal form M prepared in example 1 was placed in an oven at 50° C. with vacuum degree of −0.1 MPa to dry for 10 hours to obtain crystals.

The X-Ray powder diffractogram, the infrared absorption spectrum, the DSC thermogram and the TGA thermogram of the crystal form are shown in FIGS. 5-8, in the present invention, it is named as crystal form N of the dabigatran etexilate mesylate.

The inventor has tested the chemical stability of the crystal form M and crystal form N under normal temperature, cold storage and freezing conditions and compared the chemical stability with crystal form I, crystal form II and semihydrate crystal form, see tests 1-3. In the tests, crystal form I, crystal form II and semihydrate crystal form are all prepared according to the method disclosed in patent document U.S. Pat. No. 7,932,273B2.

Test 1 stability data under 25° C. for 6 months (see table 5)

TABLE 5

| | Crystal form I | | Crystal form II | | Semihydrate crystal form | | Crystal form M | | Crystal form N | |
| --- | --- | --- | --- | --- | --- | --- | --- | --- | --- | --- |
| | Major peak | degradant impurity RRT = 1.62 | Major peak | degradant impurity RRT = 1.62 | Major peak | degradant impurity RRT = 1.62 | Major peak | degradant impurity RRT = 1.62 | Major peak | degradant impurity RRT = 1.62 |
| 0 month | 99.690 | 0.097 | 99.646 | 0.008 | 99.847 | 0.024 | 99.711 | 0.039 | 99.701 | 0.038 |
| 1 month | 99.604 | 0.158 | 99.493 | 0.114 | 99.707 | 0.067 | 99.632 | 0.120 | 99.631 | 0.121 |
| 2 months | 99.574 | 0.243 | 99.408 | 0.244 | 99.613 | 0.114 | 99.614 | 0.150 | 99.618 | 0.152 |
| 3 months | 99.468 | 0.308 | 99.290 | 0.332 | 99.587 | 0.209 | 99.595 | 0.170 | 99.601 | 0.175 |
| 4 months | 99.308 | 0.360 | 99.069 | 0.441 | 99.447 | 0.321 | 99.582 | 0.180 | 99.580 | 0.181 |
| 5 months | 99.309 | 0.461 | 99.029 | 0.533 | 99.334 | 0.367 | 99.574 | 0.190 | 99.572 | 0.193 |
| 6 months | 99.220 | 0.522 | 98.911 | 0.598 | 99.254 | 0.415 | 99.541 | 0.212 | 99.536 | 0.221 |

Test 2 stability data under 5° C. for 6 months (see table 6)

TABLE 6

| | Crystal form I | | Crystal form II | | Semihydrate crystal form | | Crystal form M | | Crystal form N | |
| --- | --- | --- | --- | --- | --- | --- | --- | --- | --- | --- |
| | Major peak | degradant impurity RRT = 1.62 | Major peak | degradant impurity RRT = 1.62 | Major peak | degradant impurity RRT = 1.62 | Major peak | degradant impurity RRT = 1.62 | Major peak | degradant impurity RRT = 1.62 |
| 0 month | 99.676 | 0.097 | 99.631 | 0.008 | 99.828 | 0.024 | 99.654 | 0.039 | 99.660 | 0.038 |
| 1 month | 99.655 | 0.100 | 99.630 | 0.015 | 99.827 | 0.035 | 99.650 | 0.039 | 99.659 | 0.038 |
| 2 months | 99.651 | 0.114 | 99.643 | 0.028 | 99.830 | 0.036 | 99.648 | 0.039 | 99.655 | 0.040 |
| 3 months | 99.652 | 0.117 | 99.640 | 0.039 | 99.826 | 0.036 | 99.651 | 0.039 | 99.652 | 0.040 |
| 4 months | 99.651 | 0.121 | 99.641 | 0.047 | 99.831 | 0.036 | 99.649 | 0.040 | 99.650 | 0.041 |
| 5 months | 99.649 | 0.129 | 99.598 | 0.059 | 99.827 | 0.036 | 99.649 | 0.041 | 99.650 | 0.041 |
| 6 months | 99.643 | 0.134 | 99.592 | 0.064 | 99.832 | 0.037 | 99.648 | 0.042 | 99.649 | 0.042 |

Test 3 stability data under −20° C. for 6 months (see table 7)

TABLE 7

| | Crystal form I | | Crystal form II | | Semihydrate crystal form | | Crystal form M | | Crystal form N | |
| --- | --- | --- | --- | --- | --- | --- | --- | --- | --- | --- |
| | Major peak | degradant impurity RRT = 1.62 | Major peak | degradant impurity RRT = 1.62 | Major peak | degradant impurity RRT = 1.62 | Major peak | degradant impurity RRT = 1.62 | Major peak | degradant impurity RRT = 1.62 |
| 0 month | 99.694 | 0.097 | 99.631 | 0.008 | 99.836 | 0.024 | 99.734 | 0.039 | 99.735 | 0.038 |
| 1 month | 99.693 | 0.098 | 99.630 | 0.010 | 99.834 | 0.023 | 99.722 | 0.038 | 99.723 | 0.038 |
| 2 months | 99.694 | 0.098 | 99.633 | 0.010 | 99.833 | 0.022 | 99.728 | 0.039 | 99.726 | 0.039 |

TABLE 7-continued

|  | Crystal form I | | Crystal form II | | Semihydrate crystal form | | Crystal form M | | Crystal form N | |
| --- | --- | --- | --- | --- | --- | --- | --- | --- | --- | --- |
|  | Major peak | degradant impurity RRT = 1.62 | Major peak | degradant impurity RRT = 1.62 | Major peak | degradant impurity RRT = 1.62 | Major peak | degradant impurity RRT = 1.62 | Major peak | degradant impurity RRT = 1.62 |
| 3 months | 99.690 | 0.097 | 99.634 | 0.011 | 99.836 | 0.023 | 99.737 | 0.040 | 99.734 | 0.038 |
| 4 months | 99.692 | 0.098 | 99.630 | 0.010 | 99.839 | 0.022 | 99.737 | 0.041 | 99.733 | 0.040 |
| 5 months | 99.691 | 0.098 | 99.632 | 0.011 | 99.840 | 0.024 | 99.739 | 0.038 | 99.734 | 0.038 |
| 6 months | 99.692 | 0.099 | 99.632 | 0.011 | 99.836 | 0.024 | 99.737 | 0.039 | 99.733 | 0.039 |

From tests 1-3, it can be seen that the crystal form M and the crystal form N of the dabigatran etexilate can be stored stable for a long time under cold storage and freezing conditions and they showed better chemical stability under normal temperature and cold storage conditions compared with the existing dabigatran etexilate crystal form I, crystal form II and the semihydrate crystal form.

In addition, the samples of crystal form M and crystal form N used in the stability tests for 6 months under different temperature were not changed, which indicate that the stability of crystal forms M and N were great.

Test 4 the stability in formulation of crystal form N

The crystal form N was placed in 95% ethanol solution, the solution was stirred for 3, 4 and 5 hours, then they were subjected to XRD measurement, the results showed that the X-Ray powder diffractograms were not changed within 5 hours. This indicate that the crystal form N is stable in the 95% ethanol solution, therefore, it has great stability in the related formulation processes.

The invention claimed is:

1. A crystal form M of the dabigatran etexilate mesylate, characterized in that the X-Ray powder diffractogram thereof has characteristic peaks at the following 2θ diffraction angles: 5.7±0.2°, 6.2±0.2°, 11.2±0.2°, 12.4±0.2°, 18.2±0.2°, 21.4±0.2°, 21.8±0.2° and 23.6±0.2°.

2. The crystal form M of the dabigatran etexilate mesylate according to claim 1, characterized in that the X-Ray powder diffractogram thereof also has characteristic peaks at the following 2θ diffraction angles: 16.3±0.2°, 22.8±0.2°, 25.0±0.2° and 27.3±0.2°.

3. The crystal form M of the dabigatran etexilate mesylate according to claim 2, characterized in that the X-Ray powder XRD diffractogram thereof also has characteristic peaks at the following 2θ diffraction angles: 8.1±0.2°, 13.0±0.2°, 17.1±0.2°, 29.0±0.2°.

4. The crystal form M of the dabigatran etexilate mesylate according to claim 3, characterized in that the relative intensities of the characteristic peaks are:

| characteristic peak 2θ (°) | relative intensity (%) |
| --- | --- |
| 5.7 ± 0.2 | 20.1 |
| 6.2 ± 0.2 | 24.0 |
| 8.1 ± 0.2 | 6.6 |
| 11.2 ± 0.2 | 48.9 |
| 12.4 ± 0.2 | 62.0 |
| 13.0 ± 0.2 | 16.6 |
| 16.3 ± 0.2 | 16.6 |
| 17.1 ± 0.2 | 17.0 |
| 18.2 ± 0.2 | 100.0 |
| 21.4 ± 0.2 | 69.4 |
| 21.8 ± 0.2 | 55.5 |
| 22.8 ± 0.2 | 27.1 |
| 23.6 ± 0.2 | 34.9 |
| 25.0 ± 0.2 | 31.4 |
| 27.3 ± 0.2 | 37.1 |
| 29.0 ± 0.2 | 6.1. |

5. A method for preparing the crystal form M of the dabigatran etexilate mesylate according to claim 1 comprising the following steps:
(1) dabigatran etexilate mesylate is added into an ethanol/ethyl acetate mixed solvent with the volume ratio of ethanol/ethyl acetate of 1:2; wherein the weight-to-volume ratio of the dabigatran etexilate mesylate to ethanol/ethyl acetate mixed solvent is 1:40; and the molar ratio of the total water content in the obtained system to the dabigatran etexilate mesylate is controlled to 1.5-10:1;
(2) the temperature is increased to 50-60° C., and the system is stirred continuously for 30-60 min to dissolve the dabigatran etexilate mesylate;
(3) the system is filtered and the filtrate is stirred to decrease the temperature to 0-25° C.;
(4) crystallization is performed at 0-25° C. for 2-18 h;
(5) crystal form M of dabigatran etexilate mesylate is obtained by filtration;
Or comprising the following steps:
(1') dabigatran etexilate mesylate is added into an alcohol, or alcohol/ketone mixed solvent or alcohol/ester mixed solvent; and the molar ratio of the total water content in the obtained system to the dabigatran etexilate mesylate is controlled to 1.5-10:1;
(2') the temperature is increased to 50-60° C., and the system is stirred continuously for 30-60 min to dissolve the dabigatran etexilate mesylate;
(3') the system is filtered and the filtrate is stirred to decrease the temperature to 0-5° C.;
(4') seed crystals are added;
(5') crystallization is performed at 0-5° C., crystal form M of dabigatran etexilate mesylate is obtained by filtration.

6. The method for preparing the crystal form M of the dabigatran etexilate mesylate according to claim 5, wherein the alcohol is C1-C4 alcohol, preferably methanol, ethanol, isopropanol or n-butyl alcohol; the ketone is C3-C5 ketone, preferably acetone, butanone or pentanone; the ester is C3-C6 ester, preferably methyl acetate, ethyl acetate or butyl acetate; the preferred solvent is ethanol, ethanol/acetone mixed solvent, ethanol/ethyl acetate mixed solvent.

7. The method for preparing the crystal form M of the dabigatran etexilate mesylate according to claim 6, characterized in that when ethanol is used as solvent, the weight-to-volume ratio of dabigatran etexilate mesylate to ethanol solvent is 1:10-100, more preferably 1:10-20.

8. The method for preparing the crystal form M of the dabigatran etexilate mesylate according to claim 6, characterized in that when ethanol/acetone mixed solvent is used as solvent, the weight-to-volume ratio of dabigatran etexilate mesylate to the mixed solvent is 1:10-100, preferably 1:10-30; the volume ratio of ethanol to acetone is 1:0.1-20, preferably 1:0.5-5.

9. The method for preparing the crystal form M of the dabigatran etexilate mesylate according to claim 6, characterized in that when ethanol/ethyl acetate mixed solvent is used as solvent, the weight-to-volume ratio of dabigatran etexilate mesylate to the mixed solvent is 1:10-100, preferably 1:10-30; volume ratio of ethanol to ethyl acetate is 1:0.1-20, preferably 1:0.5-5.

10. A crystal form N of the dabigatran etexilate mesylate, characterized in that the X-Ray powder diffractogram thereof has characteristic peaks at the following 2θ diffraction angles: 6.0±0.2°, 11.8±0.2°, 18.2±0.2°, 21.6±0.2°, 24.4±0.2°, 27.7±0.2° and 29.7±0.2°.

11. The Crystal form N of the dabigatran etexilate mesylate according to claim 10, characterized in that the X-Ray powder diffractogram thereof also has characteristic peaks at the following 2θ diffraction angles: 10.7±0.2°, 16.1±0.2° and 20.3±0.2°.

12. The Crystal form N of the dabigatran etexilate mesylate according to claim 11, characterized in that the relative intensities of the characteristic peaks are:

| Characteristic peak 2θ (°) | Relative intensity (%) |
| --- | --- |
| 6.0 ± 0.2 | 23.0 |
| 10.7 ± 0.2 | 10.4 |
| 11.8 ± 0.2 | 64.8 |
| 16.1 ± 0.2 | 4.3 |
| 18.2 ± 0.2 | 39.6 |
| 20.3 ± 0.2 | 7.0 |
| 21.6 ± 0.2 | 100.0 |
| 24.4 ± 0.2 | 44.3 |
| 27.7 ± 0.2 | 17.0 |
| 29.7 ± 0.2 | 10.9. |

13. A method for preparing the crystal form N of the dabigatran etexilate mesylate according to claim 10 comprising drying the crystal form M of the dabigatran etexilate mesylate characterized in that the X-Ray powder diffractogram thereof has characteristic peaks at the following 2θ diffraction angles: 5.7±0.2°, 6.2±0.2°, 11.2±0.2°, 12.4±0.2°, 18.2±0.2°, 21.4±0.2°, 21.8±0.2° and 23.6±0.2° under a vacuum degree of −0.06 Mpa-−0.1 Mpa to obtain the crystal form N of the dabigatran etexilate mesylate; the temperature for drying is preferably 20-50° C.; the time is preferably 10-100 hours.

14. A pharmaceutical composition comprising the crystal form M of the dabigatran etexilate mesylate characterized in that the X-Ray powder diffractogram thereof has characteristic peaks at the following 2θ diffraction angles: 5.7±0.2°, 6.2±0.2°, 11.2±0.2°, 12.4±0.2°, 18.2±0.2°, 21.4±0.2°, 21.8±0.2° and 23.6±0.2° or the crystal form N of the dabigatran etexilate mesylate according to claim 10.

15. A method of anticoagulation, comprising administrating an effective amount of crystal form M of the dabigatran etexilate mesylate according to claim 1 or the crystal form N of the dabigatran etexilate mesylate according to claim 10.

* * * * *